United States Patent [19]

Semm

[11] Patent Number: 5,387,224
[45] Date of Patent: Feb. 7, 1995

[54] ADHESION PROPHYLAXIS

[75] Inventor: Kurt Semm, Kiel, Germany

[73] Assignee: WISAP Gesellschaft fur wissenschaftlichen Apparatebau, Sauerlach, Germany

[21] Appl. No.: 976,930

[22] Filed: Nov. 18, 1992

[30] Foreign Application Priority Data

Nov. 19, 1991 [DE] Germany .............................. 4138100

[51] Int. Cl.⁶ ............................................. A61B 17/00
[52] U.S. Cl. ........................................ 606/191; 606/192; 600/37
[58] Field of Search ............................... 600/29–32, 600/37; 623/1; 604/104–109; 606/191–200

[56] References Cited

U.S. PATENT DOCUMENTS

| | | | |
|---|---|---|---|
| 3,447,533 | 6/1969 | Spicer | 600/32 |
| 4,798,205 | 1/1989 | Bonomo et al. | 606/192 |
| 5,167,614 | 12/1992 | Tessman et al. | 623/1 |
| 5,176,692 | 12/1991 | Wilk et al. | 606/191 |
| 5,183,465 | 2/1993 | Xanthakos et al. | 604/106 |
| 5,195,507 | 3/1993 | Bilweis | 606/191 |
| 5,269,753 | 12/1993 | Wilk | 606/192 |

Primary Examiner—Randall L. Green
Assistant Examiner—Rob Clarke
Attorney, Agent, or Firm—Keck, Mahin & Cate

[57] ABSTRACT

The invention relates to a mechanical adhesion prophylaxis for endoscopy, in which a double-walled sheet is rolled onto a sheet applicator and introduced into the body cavity. In the body cavity the double-walled sheet is inflated in the manner of an air cushion and consequently prevents postoperative adhesion of deperitonized areas. The air cushion-like adhesion prophylaxis can be fixed in the body cavity by fixing areas.

15 Claims, 1 Drawing Sheet

ADHESION PROPHYLAXIS

BACKGROUND OF THE INVENTION

The invention relates to a mechanical adhesion prophylaxis for avoiding postoperative adhesion.

Whilst with respect to the treatment of organs in the abdominal cavity operating procedures have reached a very high standard, there is still no reliable method to avoid postoperative adhesion in the abdominal and omental regions. As yet no method has led to a success rate, which in the case of a relaparotomy, i.e. a repeated opening of the abdomen, has allowed a successful adhesiolysis, i.e. removing abdominal and omental adhesions. Thus, in general surgery, the standard procedure has been only to use adhesiolysis in the case of extreme symptoms, e.g. subileus or repeated acute abdominal obstruction. The relapse rate is approximately 80%. This means that there is a risk of a further increase in the number of adhesions following such an operation.

SUMMARY OF THE INVENTION

The object of the invention is therefore to provide an adhesion prophylaxis for avoiding postoperative adhesion, which prevents an adhesion and growing together of peritonized tissue surfaces and which can in particular be relatively simply used in endoscopic abdominal surgery.

This object is achieved by a mechanical adhesion prophylaxis for endoscopic abdominal surgery, which is constructed with an inflatable cushion-like sleeve, an inflating area located on the sleeve for blowing up the latter and at least one fixing area for fixing the sleeve to a body tissue of a body cavity, in which adhesion prophylaxis is to be applied. Advantageous further developments of the invention form the subject matter of subclaims.

According to the invention, following the operation and in particular after adhesiolysis, i.e. a mechanical blunt or sharp separation of adhered peritoneum parts by means of scissors and knife temporarily a plastic sheet is inserted between engaging tissue parts. This plastic sheet prevents adhesion of the peritonized abdominal, omental and peritoneal surfaces, which immediately reappear due to the exuding of fibrin, hystocites and fibrocytes following such an operation. After a time of a few hours to days, preferably 48 hours, the plastic sheet is removed. The sheet must be inert, i.e. have no toxic properties.

The sheets are applied in a pneumoperitoneum by means of a special application set, e.g. by means of a 10 mm sheet applicator according to German patent application P 41 32 855.8. The spreading out of the sheet in the abdominal cavity following the unwinding of the insertion rod is not technically simple and therefore takes up a considerable amount of time. The insertion of the sheet following adhesiolysis is facilitated in that the sheet is constructed as an inflatable, cushion-like balloon. It then assumes the predetermined shape in the abdominal cavity generally inflated by carbon dioxide gas, such as is e.g. the case in an air mattress.

In a similar manner to an air mattress the intraabdominal sheet is compartmentalized and thus adapted to the abdominal cavity shape or individual sections thereof, so that it spreads out in the abdominal cavity in accordance with its predetermined shape, without many manipulations being necessary for this purpose. In most cases this obviates the need for fixing the balloon, which can be limited to special cases.

Due to the intermittent drawing off of the carbon dioxide gas from the balloon and subsequent refilling, the effect of mechanical peritoneal separation is increased by the balloon. After a given time the sheet or the balloon can be removed at the indicated point through a trocar passing through the abdominal wall.

This adhesion prophylaxis has primarily been developed for the abdominal cavity. However, it is also usable for other body cavities. However, the outer contour of the balloon or plastic bag must be adapted to the corresponding cavity as regards shape and size. A specially constructed, particularly wind-up or foldable form for the inflating element for the gas ensures that the sheet can be removed without any separate manipulation.

Through the use of the mechanical adhesion prophylaxis it is possible to greatly reduce the relapse rate compared with conventional adhesiolysis per laparotomiam.

Whereas simple single-layer adhesion sheets, after estimating the approximately necessary sheet size, can be trimmed with scissors prior to application, inflatable flat balloons are produced in different sizes, which are inserted in the abdomen in the same way as the sheet. The sheet can have an inflating element and e.g. is pumped up through a Veress needle. However, it is also possible to insert a pumping instrument, e.g. a hose through an appropriately positioned trocar cannula and at its distal end it has an adapter connection complimentary to the inflating element.

Above and below the applied flat balloon it may be advantageous to in each case insert a Robinson catheter or similar draining means, so as on the one hand to aid the outflow of secretions and on the other, in the case of any suture inadequacy, e.g. of intestinal sutures, immediately obtain the necessary information concerning the secretion bag.

After 48 hours the sheet or inflated flat balloon can be released from its fixing points by means of a second-look pelviscopy and can be completely drawn out through the abdominal wall using a diameter 10 mm trocar cannula.

Since the use of a flat balloon may render unnecessary the fixing of the adhesion prophylaxis, the operations of fixing during application or release on removing the flat balloon from the body cavity are rendered unnecessary.

BRIEF DESCRIPTION OF THE DRAWINGS

The invention is described in greater detail hereinafter relative to the drawings, wherein show.

DESCRIPTION OF THE PREFERRED EMBODIMENT

Figure 1:
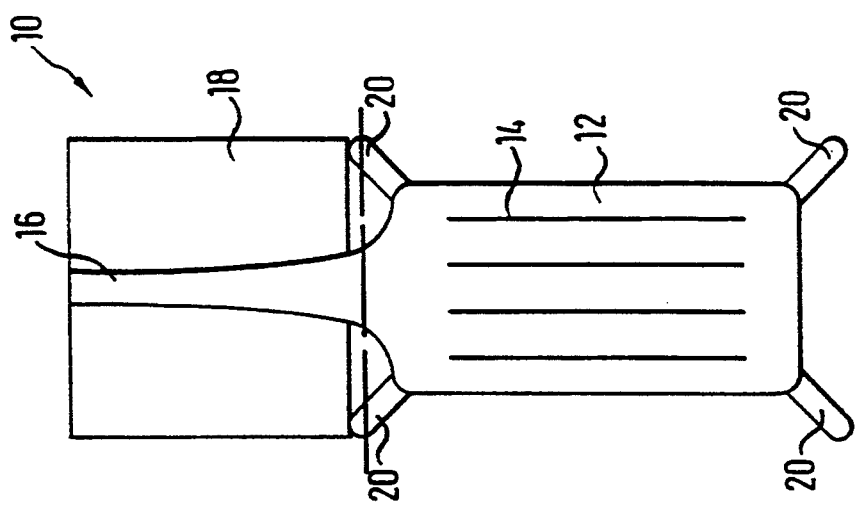
FIG. 1 A plan view of an antiadhesion bag for the major pelvis.

The antiadhesion bag or vessel 10 shown in FIG. 1 comprises an elongated air cushion 12 with a substantially rectangular shape, which has stiffening plates 14 running parallel to the longitudinal axis in the manner of an air mattress. One end face issues into an inflating channel 16, which is welded to a four-layer sheet 18, to obtain greater stiffness. At its four corners the air cushion 12 has fixing plates 20, with which it is possible to fix the antiadhesion bag 10 in the pelvic region or in the abdominal cavity. The antiadhesion bag or vessel is made from plastic sheets, whose edges are welded together. The plastic sheet material is non-toxic, tissue-friendly, tear-resistant, highly flexible and only stores a little water.

Figure 2:
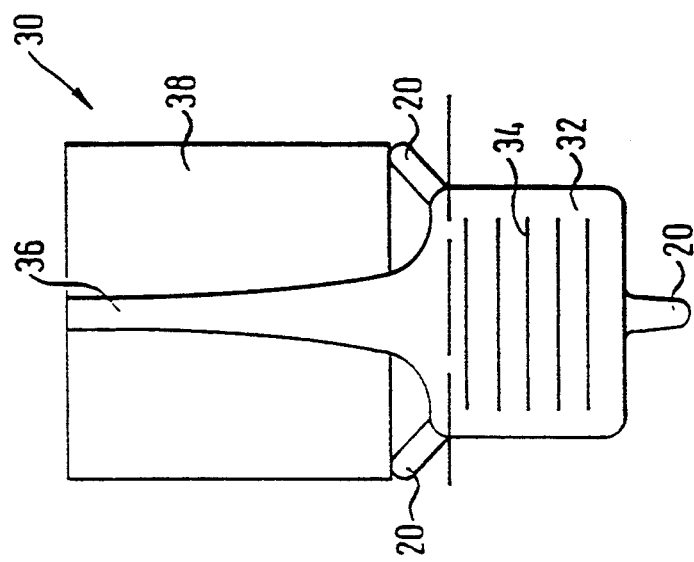
FIG. 2 An antiadhesion bag for the minor pelvis.

FIG. 2 shows an antiadhesion bag 30 for the minor pelvis. Compared with the air cushion 12 of FIG. 1, it has a smaller air cushion 32, which is essentially shaped like a bag. The air cushion 32 is provided with stiffening plates 34 arranged transversely to the longitudinal axis of the antiadhesion bag 30 in the manner of an air mattress and has an inflating hose 36, which passes in funnel-shaped manner into the air cushion 32. The inflating hose 36 is e.g. welded to a four-layer sheet 38 in order to increase the stability of the inflating hose or tube 36.

The stiffening of the inflating hoses or tubes 16, 36 by the sheets 18, 38 shown in FIGS. 1 and 2 is brought about in such a way with the air cushion 12, 32, that towards the bottom a funnel-shaped opening inflow area for the medium to be introduced is formed. Thus, centrally a tube is formed. The lateral flat regions are used for stabilization purposes.

The antiadhesion bags or balloons can be inflated by means of a hose to be separately introduced through the trocar cannula and which is connected to the opening area of the inflating hose 16, 36. Alternatively the balloon end having the inflating channel 16 or 36 could be led out through an appropriately positioned trocar cannula.

The introduction of an antiadhesion bag into the pneumoperitoneum is as easy as the application of an individual sheet. Thus, the antiadhesion bags 10, 30 can be rolled up onto a longitudinally slotted sheet applicator and can be introduced through the trocar cannula. The fold line for rolling up the applicator is indicated in broken form and is approximately at the end of the opening area of the inflating hose 16, 36.

Instead of having four sheet layers with corresponding welding both to the hose or tube and to the bag-like air cushion, it would also be possible to use a stronger, stabilizing sheet in the stiffening area of the inflating hose 16, 36.

The lengths of the bags and supply areas (inflating hose) could obviously vary as a function of anatomical and operative circumstances. Generally the antiadhesion bags are kept in stock in different shapes for different purposes.

What is claimed is:

1. A mechanical adhesion prophylaxis adapted for being rolled up onto a slotted applicator and for being unrolled for placing inside a closed body cavity during endoscopic abdominal surgery comprising at least two sheets interconnected at least in a marginal area thereof, forming an inflatable, cushion-like sleeve (12), an inflating area (16) for inflating the sleeve (12) located on the sleeve (12), at least one fixing area (20) for fixing the sleeve (12) to body tissue of a body cavity, to which the adhesion prophylaxis (10) is to be applied, and a for folding the adhesion prophylaxis line at which the adhesion prophylaxis is rolled up onto the slotted applicator.

2. A mechanical adhesion prophylaxis according to claim 1, wherein the sleeve (12) is constructed as a flat stretched balloon.

3. A mechanical adhesion prophylaxis according to claim 2, wherein the fixing areas (20) are located at corner areas of the flat balloon (12).

4. A mechanical adhesion prophylaxis according to claim 2, wherein the flat balloon (12) comprises at least two sheets interconnected at least in the marginal area.

5. A mechanical adhesion prophylaxis according to claim 4, wherein the sheets are welded together.

6. A mechanical adhesion prophylaxis according to claim 2, wherein the flat balloon (12) is compartmentalized in the manner of an air mattress by stiffening plates (14).

7. A mechanical adhesion prophylaxis according to claim 2, wherein the flat balloon (12) has an outer contour, which substantially corresponds to the contour of the body cavity to which the adhesion prophylaxis (10) is to be applied.

8. A mechanical adhesion prophylaxis according to claim 1, wherein the fixing areas (20) are constructed as plates.

9. A mechanical adhesion prophylaxis according to claim 1, wherein the sleeve (12) is elongated and has stiffening plates (14) parallel to its longitudinal axis.

10. A mechanical adhesion prophylaxis according to claim 1, wherein the sleeve (12) is made from a tear-resistant, tissue-friendly plastic sheet, which only stores little water.

11. A mechanical adhesion prophylaxis according to claim 1, wherein the inflating area (16, 36) is constructed as an inflating hose.

12. A mechanical adhesion prophylaxis according to claim 11, wherein the inflating hose (16, 36) passes in funnel-shaped manner into the sleeve (12, 32).

13. A mechanical adhesion prophylaxis according to claim 1, wherein the fixing areas (20) have clips for fixing to the body tissue.

14. A mechanical adhesion prophylaxis according to claim 1, wherein the fixing areas (20) are constructed as sheet strips.

15. A mechanical adhesion prophylaxis as claimed in claim 1, wherein said folding line is arranged approximately at an end of said inflating area of said cushion-like sleeve.

* * * * *